US008790662B2

(12) United States Patent
Spellberg et al.

(10) Patent No.: US 8,790,662 B2
(45) Date of Patent: Jul. 29, 2014

(54) METHODS FOR TREATING REFRACTORY INFECTIONS IN NEUTROPENIC INDIVIDUALS

(75) Inventors: Brad J. Spellberg, Rancho Palos Verdes, CA (US); Ashraf S. Ibrahim, Irvine, CA (US); John E Edwards, Jr., Palos Verdes Estates, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 13/418,263

(22) Filed: Mar. 12, 2012

(65) Prior Publication Data

US 2012/0171175 A1    Jul. 5, 2012

Related U.S. Application Data

(63) Continuation of application No. 11/340,163, filed on Jan. 25, 2006, now abandoned.

(60) Provisional application No. 60/647,082, filed on Jan. 25, 2005.

(51) Int. Cl.
| | |
|---|---|
| *A61K 39/00* | (2006.01) |
| *A61K 39/38* | (2006.01) |
| *A01N 63/00* | (2006.01) |
| *A01N 65/00* | (2009.01) |
| *A01N 63/04* | (2006.01) |

(52) U.S. Cl.
USPC ............. 424/274.1; 424/184.1; 424/93.1; 424/93.7; 424/93.5

(58) Field of Classification Search
CPC ... A61K 35/15; A61K 38/1761; A61K 23/00; A61K 35/28; A61K 45/06
See application file for complete search history.

(56) References Cited

U.S. PATENT DOCUMENTS 8,252,587 B2 * 8/2012 Fong et al. .................... 435/372

OTHER PUBLICATIONS

Mullick et al., Infection and Immunity, 2004; 72(1): 414-429.*
Vereecque et al., British Journal of Haematology, 2000; 108: 825-831.*
Leftwich et al., Cancer Research, 1986; 46: 3789-3792.*
Gaugler et al., British Journal of Haematology, 2001; 113: 940-950.*
Koutna et al., Scripta Medica, 2003; 76(3): 163-172.*
Spellberg, B. J. et al. in 6th American Society for Microbiology Conference on Candida and Candidiasis (Tampa, FL, 2002) Abstract Only.

Alavi, J. B. et al. "A randomized clinical trial of granulocyte transfusions for infection in acute leukemia" *N Eng J Med* 296: 706-711 (1977).
Athens, "Leukokinetic studies. IV. The total blood, circulating and marginal granulocyte pools and the granulocyte turnover rate in normal subjects" *J Clin Invest* 40:989-995 (1961).
Athens, et al. "Leukokinetic studies. XI. Blood granulocyte kinetics in poliycythemia vera, infection and myelofibrosis" *J. Clin. Invest.* 44: 778-788 (1965).
Bartova et al., "The influence of the cell cycle, differentiation and irradiation on the nuclear location of the abl, bcr and c-myc genes in human leukemic cells," Leukemia Research, 24:233-243 (2000).
Bodey, G. P., Buckley, M., Sathe, Y. S. & Freireich, E. J. "Quantitative relationships between circulating leukocytes and infection in patients with acute leukemia" *Annals of Internal Medicine* 64: 328-340 (1966).
Brieland, J. et al. "Comparison of pathogenesis and host immune responses to Candida glabrata and Candida albicans in systemically infected immunocompetent mice" *Infection and Immunity* 69: 5046-5055 (2001).
Caesar-Ton That et al., "A monoclonal antibody to Candida albicans enhances mouse neutrophil candidacidal activity" *Infect. Immun.* 65(12): 5354-5357 (1997).
Case records of the Massachusetts General Hospital. "Case records of the Massachusetts General Hospital. Weekly clinicopathological exercises. Case 40-1998. A 49-year-old woman with thrombotic thrombocytopenic purpura and severe dyspnea during plasmapheresis and transfusion" *N Engl J Med* 339(27): 2005-2012 (1998).
Chen, L. et al. "Impaired liver regeneration in mice lacking methionine adenosyltransferase 1A" *Faseb J* 18: 914-916 (2004).
Clemons and Stevens "Efficacy of the partricin derivative SPA-S-753 against systemic murine candidosis" *J. Antimicrob Chemother* 47:183-186 (2001).
Cohen, D., Weinstein, H., Mihm, M. & Yankee, R. "Nonfatal graft-versus-host disease occurring after transfusion with leukocytes and platelets obtained from normal donors" *Blood* 53: 1053-1057 (1979).
Collins et al, "Normal functional characteristics of cultured human promyelocytic leukemia cells (HL-60) after induction of differentiation by dimethylsulfoxide" *J Exp Med* 149:969-974 (1979).
Craddock et al. "The dynamics of leukopenia and leukocytosis" *Ann Intern Med* 52:281-294 (1960).

(Continued)

*Primary Examiner* — Vanessa L Ford
*Assistant Examiner* — Lakia Tongue
(74) *Attorney, Agent, or Firm* — Jones Day

(57) ABSTRACT

The invention is based, in part, on the discovery of a novel cell-based immunotherapy that can recapitulate neutrophil functions in neutropenic individuals afflicted with a microbial infection. The therapeutic methods of the invention are broadly applicable to treat any infection in a neutropenic individual, including infections caused by bacteria, fungi, protozoa, and viruses. The methods of the invention represent a practical, rapid cell-based immunotherapy for refractory infections comprising compositions of activated, irradiated HL-60 cells.

6 Claims, 8 Drawing Sheets
(1 of 8 Drawing Sheet(s) Filed in Color)

(56) References Cited

OTHER PUBLICATIONS

Dancey et al., "Neutrophil kinetics in man" *J. Clin. Invest* 58:705-715 (1976).
Dipietrantonio, A., Hsieh, T. C. & Wu, J. M. "Differential effects of retinoic acid (RA) and N-(4-hydroxyphenyl) retinamide (4-HPR) on cell growth, induction of differentiation, and changes in p34cdc2, Bcl-2, and actin expression in the human promyelocytic HL-60 leukemic cells" *Biochem Biophys Res Commun* 224: 837-842 (1996).
Glasser, L. "Effect of storage on normal neutrophils collected by discontinuous-flow centrifugation leukapheresis" *Blood* 50: 1145-1150 (1977).
Herzig, R. H., Herzig, G. P., Graw, R. G., Jr., Bull, M. I. & Ray, K. K. "Successful granulocyte transfusion therapy for gram-negative septicemia. A prospectively randomized controlled study" *N Eng J Med* 296: 701-705 (1977).
Hua et al., "Evaluation of the expression of NADPH oxidase components during maturation of HL-60 cells to neutrophil lineage" *J. Leukoc Biol.* 68:216-224 (2000).
Huestis, D. W. & Glasser, L. "The neutrophil in transfusion medicine" *Transfusion* 34: 630-646 (1994).
Kovacicova, G. et al. "Prospective study of fungaemia in a single cancer institution over a 10-y period: aetiology, risk factors, consumption of antifungals and outcom. in 140 patients" *Scand J Infect Dis* 33: 367-374 (2001).
Lehmbecher, T., Groll, A. H. & Chanock, S. J. "Treatment of fungal infections in neutropenic children" *Curr Opinion Ped* 11: 47-55 (1999).
Leibovici, L., Drucker, M., Samra, Z., Konisberger, H. & Pitlik, S. D. "Prognostic significance of the neutrophil count in immunocompetent patients with bacteraemia" *QJM* 88: 181-189 (1995).
Levin, R. H. et al. "Persistent mitosis of transfused homologous leukocytes in children receiving anti-leukemic therapy" *Science* 142: 1305-1307 (1963).
Louria, DB "Canida infections in experimental animals" *Candidiasis*. Bodey GP, and Fainstein V, (eds). New York: Raven Press, 1985, 29-51.
Lowenthal, R. M. et al., "Granulocyte transfusions in treatment of infections in patients with acute leukaemia and aplastic anaemia." *Lancet* 1: 353-358 (1975).
Malik, I. A., Moid, I., Aziz, Z., Khan, S. & Suleman, M. "A randomized comparison of fluconazole with amphotericin B as empiric antifungal agents in cancer patients with prolonged fever and neutropenia" *Am J Med* 105: 478-483 (1998).
Marsh, J. C., Boggs, D. R., Cartwright, G. E. & Wintrobe, M. M. "Neutrophil kinetics in acute infection" *J Clin Invest* 46: 1943-1953 (1967).
Martino, P. et al. "Candida colonization and systemic infection in neutropeni, patients. A retrospective study" *Cancer* 64: 2030-2034. (1989).
Matzner, Y., Gavison, R., Rachmilewitz, E. A. & Fibach, E. "Expression of granulocytic functions by leukemic promyelocytic HL-60 cells: differential induction by dimethylsulfoxide and retinoic acid" *Cell Differ* 21: 261-269 (1987).
Netea et al., "Increased susceptibility of TNF-alpha lymphotoxin-alpha double knockout mice to systemic candidiasis through impaired recruitment of neutrophils and phagocytosis of *Candida albicans*" *J. Immonol.* 163:1498-1505 (1999).
Nucci, M. et al. "Fungal infections in neutropenic patients. A 8-year prospective study" *Rev Inst Med Trop Sao Paulo* 37: 397-406. (1995).
Pagano, L. et al. "Retrospective study of candidemia in patients with hematological malignancies. Clinical features, risk factors and outcome of 76 episodes" *Eur J Haematol* 63: 77-85. (1999).
Rhyne, A. L. & Steel, R. G. "A multiple comparisons sign test: all pairs of reatments" *Biometrics* 23: 539-549 (1967).
Ribeiro, P. et al. "Candidemia in acute leukemia patients" *Support Care Cancer* 5(3):249-251(1997).
Roesler and Emmendorffer, "Diagnosis of chronic granulomatous disease" *Blood* 78:1387-1389.
Roesler et al. "Diagnosis of chronic granulomatous disease and of its mode of inheritance by dihydrorhodamine 123 and flow microcytofluorometry" *Eur. J. Pediatr* 150:161-165 (1991).
Schwarzenberg, I., Mathe, G., de Grouchy, J. & al., "White blood cell transfusions" *Israel Journal of Medical Science* 1: 925-956 (1965).
Spellberg, B. J. et al. "Parenchymal organ, and not splenic, immunity correlates with host survival during disseminated candidiasis" *Infect Immun* 71: 5756-5764 (2003).
Spelberg et al., "A phagocytic cell line markedly improves survival of infected neutropenic mice" *J. Leukoc Biol* 78:338-344 (2005).
Tonn, T., Becker, S., Esser, R., Schwabe, D. & Seifried, "E. Cellular immunotherapy of malignancies using the clonal natural killer cell line NK-92" *J Hematother Stem Cell Res* 10: 535-44 (2001).
Valerius et al., "FcalphaRI (CD89) as a novel trigger molecule for bispecific antibody therapy" *Blood* 90(11): 4485-4492 (1997).
van Spriel, AB et al. "Effective phagocytosis and killing of *Candida albicans* via targeting FcgammaRI (CD64) or FcalphaRI (CD89) on neutrophils" *J. Infect. Dis.* 179(3): 661-669 (1999).
Van t Wout, J. W., Mattie, H. & van Furth, R. "Comparison of the efficacies of amphotericin B, fluconazole, and itraconazole against a systemic *Candida albicans* infection in normal and neutropenic mice" *Antimicrob Agents Chemother* 33: 147-151 (1989).
Waldorf, A. R., Heide, C. & Vedros, N. A. "Murine model of pulmonary mucormycosis in cortisone-treated mice" *Sabouraudia* 20: 217-24 (1982).

\* cited by examiner

METHODS FOR TREATING REFRACTORY INFECTIONS IN NEUTROPENIC INDIVIDUALS

This application is a continuation of U.S. application Ser. No. 11/340,163, now abandoned, which claims the benefit of priority of U.S. Provisional Application Ser. No. 60/647,082, filed Jan. 25, 2005, the entire contents of each aforementioned application are incorporated herein by reference.

This invention was made with government support under grant numbers R03 AI054531, R01 AI19990 and K08 AI060641 awarded by the National Institutes of Health. The United States Government may have certain rights in this invention.

BACKGROUND OF THE INVENTION

The present invention relates generally to treatment of refractory microbial infections and, more specifically, to a method and composition for cell-based immunotherapy that can recapitulate neutrophil functions in neutropenic individuals afflicted with a microbial infection.

*Candida* is a major cause of morbidity and mortality in patients with cancer or neutropenia. *Candida* is an opportunistic fungal pathogen that has become a major cause of nosocomial infections in the United States and worldwide. *Candida* species are now the fourth most frequent nosocomial bloodstream isolates, surpassing the incidence of bacteremia caused by *Escherichia coli* or *Klebsiella* species.

Neutropenia is a major risk factor for the development of disseminated candidiasis. Neutropenia refers to an abnormally low number of neutrophils in the blood. Neutrophils, a type of white blood cell, help fight bacterial infections. A recent survey found that the incidence of disseminated candidiasis in patients with cancer was 70 per 100,000 people in the city of San Francisco, ten-fold higher than the overall population-based incidence. Several other studies have reported an overall incidence of disseminated candidiasis of 2-6% in patients with cancer or neutropenia. Therefore, approximately 28,000 to 84,000 cases of disseminated candidiasis occur per year in the 1.4 million cancer patients in the United States.

Even with antifungal therapy, disseminated candidiasis has an unacceptable attributable mortality of 50% in myeloablated patients. The mortality of *Candida* sepsis is also greater than 50%, and is therefore higher than the mortality from sepsis due to *Pseudomonas aeruginosa*, *Staphylococcus aureus*, or *E. coli*. Furthermore, resistance to conventional antifungal therapies among *Candida* isolates is rising, increasing the need for therapeutic modalities for candidal infections, in particular for patients with cancer or neutropenia.

The primary predictor of survival of neutropenic patients with hematogenously disseminated fungal infections is the duration of neutropenia rather than the type and dose of antifungal given. Thus, strategies designed to shorten the duration of neutropenia would logically improve survival. Unfortunately, while administration of myeloid growth factors, such as granulocyte-colony-stimulating-factor (G-CSF), decreases the incidence of infection by shortening the duration of neutropenia, it does not improve survival once infections develop. This lack of efficacy is likely because the effect of a growth factor depends on the ability of a marrow-ablated host to rapidly produce new phagocytes.

Since survival of hematogenously disseminated infections is linearly related to the patient's granulocyte count, exogenous replacement of phagocytes would seem to offer tremendous potential in the therapy of invasive fungal infections. Although granulocyte transfusion is a logical therapeutic option for neutropenic patients with refractory infections, significant technical barriers have prevented its wide-spread use. First, harvesting of sufficient neutrophils to mediate a protective effect is difficult to achieve. Second, the harvesting procedure can cause hemolysis, anaphylaxis, and intravascular volume shifts in donors. Third, ex vivo neutrophils undergo rapid apoptosis, and very quickly lose their ability to chemotax and to kill phagocytized organisms. Notably, this loss of microbicidal activity is particularly severe for killing of *Candida* as compared to smaller bacterial organisms. Fourth, clinically significant numbers of red blood cells, lymphocytes, platelets, and donor alloantibodies inevitably contaminate even the most pure neutrophil harvests. Therefore, the donor pool is limited by the need to cross-match blood types, and neutropenic recipients may be at risk for graft-versus-host disease (GVHD) from transfused lymphocytes. Of particular importance is that GVHD seen in recipients of granulocyte transfusions is strictly caused by lymphocyte contamination of the transfusate, as phagocytes do not mediate GVHD by themselves.

Thus, there exists a need to garner the therapeutic benefit of neutrophil transfusions but avoid the above obstacles. The present invention satisfies this need and provides related advantages as well.

SUMMARY OF THE INVENTION

The invention is based, in part, on the discovery of a novel cell-based immunotherapy that can recapitulate neutrophil functions in neutropenic individuals afflicted with a microbial infection. The therapeutic methods of the invention are broadly applicable to treat any infection in a neutropenic individual, including infections caused by bacteria, fungi, protozoa, and viruses. The methods of the invention represent a practical, rapid cell-based immunotherapy for refractory infections comprising compositions of activated, irradiated HL-60 cells.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
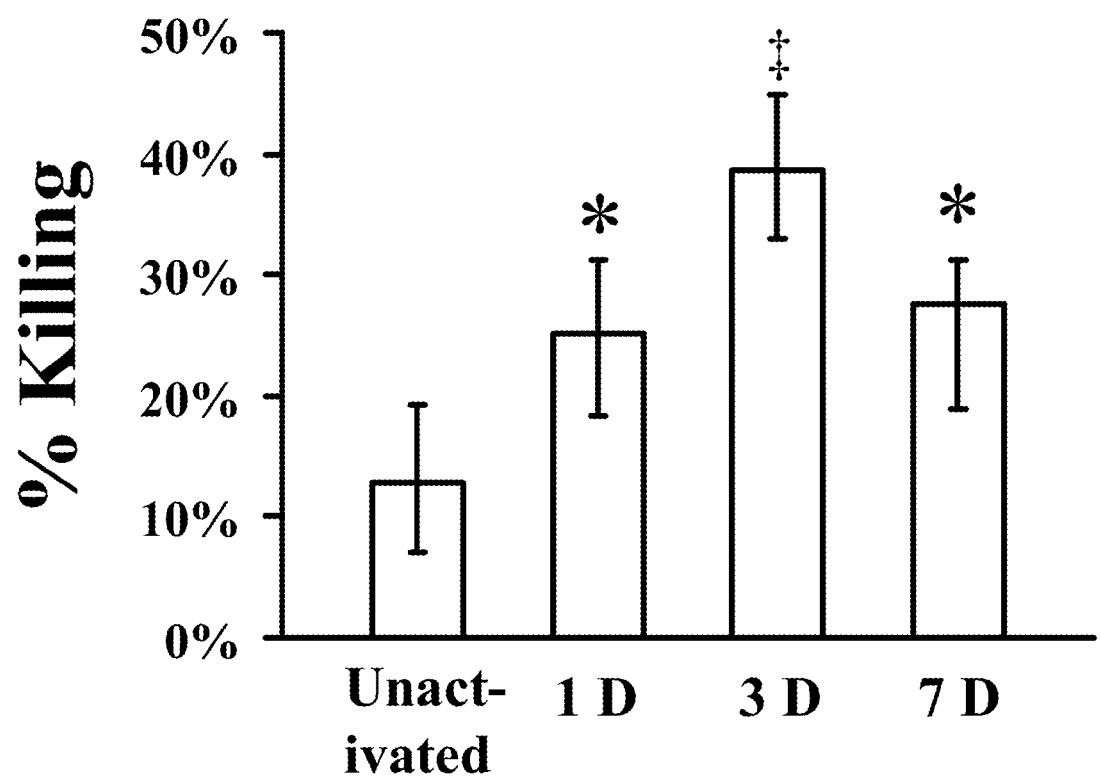
FIG. 1 demonstrates that shorter duration of HL-60 activation results in significant killing of *C. albicans*.

The invention is based, in part, on the discovery of a novel cell-based immunotherapy that can recapitulate neutrophil functions in neutropenic individuals afflicted with a microbial infection. The therapeutic compositions and methods of the invention are broadly applicable to treat any infection in a neutropenic individual, including infections caused by bacteria, fungi, protozoa, and viruses. The invention compositions of activated, irradiated HL-60 cells represent a practical, rapid cell-based immunotherapy for refractory infections.

As disclosed herein, the administration of activated, irradiated HL-60 cells to neutropenic subjects afflicted with an infection caused by, for example, bacteria, fungi, protozoa, or virus, can effect enhanced clearance of tissue microbial burden and improve survival. As exemplified herein, the administration of activated, irradiated HL-60 cells to neutropenic, candidemic subjects can effect enhanced clearance of tissue fungal burden and improve survival. Furthermore, while exemplified and disclosed with an HL-60 cell line, the invention covers any immortal phagocytic cell-line that can be activated and irradiated to have equivalent or superior efficacy in practicing the invention methods.

The present invention provides a method for treating a hematogenously disseminated fungal infection in a neutropenic individual by administering a therapeutically effective amount of an activated and irradiated phagocytotic cell line to the individual. The methods of the invention are further applicable to any infection in a subject afflicted with neutropenia, including, bacteria, fungi, protozoa, and virus. As exemplified herein, the administration of an activated and irradiated HL-60 cell line can treat a condition associated with neutropenia, such as a hematogenously disseminated fungal infection, by compensating for the individual's lack of sufficient levels of neutrophils to mount neutrophil mediated host defense functions necessary to fight the condition.

The immortal phagocytic cell-line used in the methods described herein is activated and irradiated prior to being administered to a neutropenic individual and serves to recapitulate the individual's neutrophil host defense functions until the individual's own phagocyte count is restored.

In a preferred embodiment, the invention further provides a method for treating neutropenia in an individual by transfusion of an effective amount of an activated and irradiated HL-60 cell line to an individual afflicted with neutropenia. In a preferred embodiment of the invention method, the neutropenia is a transient rather than a chronic condition. In this preferred embodiment, the restoration of neutrophil levels serves to mount the individuals neutrophil mediated host defense mechanisms, which subsequently assume their natural role in defeating the underlying condition.

In a further preferred embodiment, the activation and irradiation of HL-60 cells provides a method to treat hematogenously disseminated fungal infection in individuals with neutropenia. However, the methods of the invention for treating neutropenia are exemplified but not limited to treating fungal infections. Rather, because neutrophils/phagocytes provide protection against and kill any type of microbe (bacteria, fungi, protozoa, and even some viruses), the methods disclosed herein are widely applicable to treat any infection occurring in an individual with a decreased phagocyte count. Similarly, while the method of the invention are particularly useful for treatment of conditions associated with a transient decrease in phagocyte count, the invention methods are also applicable to chronic conditions where the phagocyte count has to be restored on a regular basis to not only recapitulate but also maintain the presence of neutrophil mediated host defense functions.

The invention also provides a therapeutic composition of an activated and irradiated HL-60 cell line that is useful for practicing the methods of the invention for treating transient neutropenia associated with a condition such as a hematogenously disseminated fungal infection. The HL-60 cells used in a therapeutic composition of the invention have been activated for at least 24 hours, at least 36 hours, at least 48 hours, at least 60 hours, at least 72 hours, at least 84 hours or more. In a preferred embodiment, the HL-60 cells have been activated for at least 72 hours or three days. The HL-60 cells incorporated into the compositions of the invention and used in the methods of the invention are activated in the presence of retinoic acid (RA) and dimethylsulfoxide (DMSO) to induce the HL-60 cells to differentiate down the way of neutrophilic lineage. While the activation is exemplified with retinoic acid (RA) and dimethylsulfoxide (DMSO), one skilled in the art will appreciate that agents that have an equivalent or superior activation effect also can be used and will know how to select such agents.

As disclosed herein, the cells used in the methods and compositions of the invention have been irradiated. The unit of absorbed dose, the rad, which is a measure of energy absorbed per gram of material can be at least 500 rads, at least 1000 rads, at least 1500 rads, at least 2000 rads, at least 2500 rads, at least 3000 rads, at least 400 rads or more. The values provided are further understood to be approximate values and can vary by 300 rads in either direction without being considered a departure from the intended dosage. In a preferred embodiment, the cells corresponding to an immortal phagocytic cell-line, for example, HL-60, have been irradiated with at least 1500 rads prior to use of the cells in the invention methods and compositions. As the skilled person will appreciate, any radiation dosage that abrogates replicative capacity while retaining antimicrobial function represents an appropriate amount of radiation for the cells used in the methods and compositions of the invention. The skilled person will be able to use the teachings and guidance provided herein to select and confirm appropriate radiation dosage for practicing any aspect of the invention.

The activated cells that make up the invention compositions and methods have physical characteristics that can be used to distinguish them from unactivated counterparts by flow cytometry. As described herein and exemplified below, the flow cytometric parameters are selected from the group comprising cell viability, cell size, and change in cell size during activation. Facile markers that can be used to distinguish activated from unactivated HL-60 cells include cell viability, cell size, and oxidative free radical formation, also correlate with in vitro killing of *C. albicans*. These physical characteristics define the compositions of the invention and can serve, inter alia, as useful quality control markers of activation as well as to identify and confirm the presence of a composition useful for practicing the claimed invention.

The activated and irradiated HL-60 cell line that is provided by the invention has broad antimicrobial activity that includes antifungal, antibacterial, antiviral or antiprotozoal activity. In a particular embodiment, the activated and irradiated HL-60 cell line has significant anti-fungal capacity. Fungi, particularly species of *Candida, Aspergillus*, and *Fusarium* are a major cause of infection-related mortality in patients with leukemia and lymphoma. *Candida* constitutes one of the major groups that cause systemic fungal infections and the medically relevant species which are most often recovered from individuals, include *C. albicans, C. tropica-*

*lis, C. glabrata, C. parapsilosis* and *C. krusei*. For example, a exemplified herein, the invention compositions, which comprise an activated and irradiated HL-60 cell line, as well as the methods provided of using an activated and irradiated HL-60 cell line of the invention, can be used to achieve anti-candidal effects. The methods and compositions of the present invention also are applicable to blood stream infections caused by bacteria, for example *P. aeruginosa* or *S. aureus*, and are particularly useful for application as an alternative therapy against resistant bacterial strains such as, for example, methicillin-resistant *S. aureus* or ciprofloxacin-resistant *P. aeruginosa*.

As described above, the methods of the invention for treating neutropenia are exemplified but not limited to treating fungal infections. Rather, because neutrophils/phagocytes provide protection against and kill any type of microbe (bacteria, fungi, protozoa, and even some viruses), the methods disclosed herein are widely applicable to treat any infection occurring in an individual with a decreased phagocyte count. Neutrophils serve as the major defense of the body against acute bacterial, fungal and protozoal infections. Neutrophils usually constitute about 45 to 75% of all white blood cells in the bloodstream. When the neutrophil count falls below 1,000 cells per microliter of blood, the risk of infection increases somewhat; when it falls below 500 cells per microliter, the risk of infection increases greatly. Without the key defense provided by neutrophils, a person has problems controlling infections and is at risk of dying from an infection.

Neutropenia can develop if neutrophils are used up or destroyed in the bloodstream faster than the bone marrow can make new ones. In the presence of cancer therapy, some allergic disorders, and some drug treatments, neutrophils are destroyed faster than they are produced. People with an autoimmune disease can make antibodies that destroy neutrophils and result in neutropenia. People with an enlarged spleen may have a low neutrophil count because the enlarged spleen traps and destroys neutrophils.

Neutropenia can also develop if the production of neutrophils in the bone marrow is reduced, as can occur in some people with cancer, viral infections such as influenza, bacterial infections such as tuberculosis, myelofibrosis, or deficiencies of vitamin B12 or folic acid. People who have received radiation therapy that involves the bone marrow may also develop neutropenia. Production of neutrophils in the bone marrow is also affected by a severe disorder called aplastic anemia in which the bone marrow may shut down production of all blood cells. Certain rare hereditary diseases also cause the number of neutrophils to decrease.

Neutropenia affects as many as one in three patients receiving chemotherapy for cancer. It is also associated with many other diseases like Lupus (SLE), Malaria, Hepatitis viruses, Barth Syndrome, Rheumatoid Arthritis, Sjogren's Syndrome, Shwachman-Diamond Syndrome, Aplastic Anemia and Myelodysplastic Syndromes, Parvovirus, Felty's Syndrome, to name just a few. Neutropenia can be a serious problem requiring prompt attention. Without proper medical care, patients may find it hard to lead normal lives. Severe cases can be life threatening. Other rare diseases like Kostmann's Syndrome (a congenital neutropenia) can evolve to leukemia and require a bone marrow transplant.

The therapeutic compositions and methods of the invention can be performed as parts of a treatment regimen that includes other components. For example, the methods and compositions described herein can be combined with administration of growth factors called colony-stimulating factors, which stimulate the production of white blood cells. The methods and compositions of the invention also can be combined with corticosteroids if the neutropenia is caused by an autoimmune reaction or with antithymocyte globulin or other types of therapy that suppresses the activity of the immune system when a disease such as aplastic anemia is present. When neutropenia is caused by another disease (such as tuberculosis or leukemia or other cancers), treatment of the underlying disease may resolve the neutropenia but the methods and compositions of the invention may still be useful to strengthen the neutrophil mediated host defenses in order to prevent infection. Furthermore, the methods and compositions of the invention can be combined with bone marrow or stem cell transplantation to treat certain serious causes of neutropenia, such as aplastic anemia or leukemia.

The invention method provides several advantages over standard treatments that involve phagocyte transfusion. By utilizing cultured, transformed cells, the possibility of contamination of the infusate by red cells, platelets, lymphocytes, or donor anti-recipient antibodies can be eliminated. Additionally, because the cell-line's population is ever-renewing, an unlimited number of phagocytes can be cultured, allowing achievement of infusion doses approximating the normal endogenous neutrophil turn-over rate. Since the protective effect of phagocyte transfusions directly correlates with the dose, creating an immortalized cell-line for administration allows for a dramatic improvement in their efficacy. Furthermore, since allogeneic phagocytes do not mediate GVHD, an immortal phagocytic cell-line will not attack host tissues. The lack of allogeneic lymphocyte contamination of the phagocytic cell-line will make infusions safer than the neutrophil transfusions described previously.

Many antimicrobial agents are known to those of skill in the art and may be useful in being part of a treatment regimen that includes the therapeutic compositions and methods of the present invention in combination with a suitable antifungal, antibacterial, antiviral or antiprotozoal agent.

Suitable antibacterial agents for combination treatment with the invention compositions and methods include Acrosoxacin, Amifloxacin, Amoxycillin, Ampicillin, Aspoxicillin, Azidocillin, Azithromycin, Aztreonam, Balofloxacin, Benzylpenicillin, Biapenem, Brodimoprim, Cefaclor, Cefadroxil, Cefatrizine, Cefcapene, Cefdinir, Cefetamet, Cefmetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Tinidazole, Tosufloxacin, Trimethoprim and salts or esters thereof.

Suitable antiprotozoal agents for combination treatment with the invention compositions and methods include Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole and salts or esters thereof.

Suitable antiviral agents for combination treatment with the invention compositions and methods include Acyclovir, Brivudine, Cidofovir, Curcumin, Desciclovir, 1-Docosanol, Edoxudine, Fameyclovir, Fiacitabine, Ibacitabine, Imiquimod, Lamivudine, Penciclovir, Valacyclovir, Valganciclovir and salts or esters thereof.

In a particular embodiment, the invention provides a method of reducing or inhibiting growth or survival of a microorganism in an environment capable of sustaining the growth or survival of the microorganism, comprising administering an effective amount of an activated and irradiated human myeloid cell line to said environment, thereby reducing or inhibiting the growth or survival of the microorganism. The methods of the invention are applicable to such diverse classes of microorganisms as fungi, gram negative bacteria, gram positive bacteria, viruses, and protozoa. In a particular embodiment, the microorganism is a pathogenic fungus. In other embodiments the microorganism belongs to the phylum candida. In a preferred embodiment, the pathogenic fungus is *Candida albicans*.

The invention also provides a method for treating a hematogenously disseminated microbial infection in an individual that encompasses transfusion of an effective amount of an activated and irradiated HL-60 cell line to the individual afflicted with a hematogenously disseminated microbial infection. As described herein, the methods of the invention are applicable to microbial infections having as their causative agent diverse microorganisms such as fungi, gram negative bacteria, gram positive bacteria, viruses, and protozoa.

In a particular embodiment, the invention provides a method for treating a hematogenously disseminated fungal infection in an individual that encompasses transfusion of an effective amount of an activated and irradiated HL-60 cell line to the individual afflicted with a hematogenously disseminated fungal infection. In a preferred embodiment, the fungal infection is candidiasis. In a particular embodiment, the candidiasis is caused by *Candida albicans*.

Also provided is method for treating neutropenia in an individual. This method of the invention encompasses transfusion of an effective amount of an irradiated and activated HL-60 cell line to an individual afflicted with neutropenia. In a preferred embodiment, the neutropenia is transient and related to an underlying microbial infection such that restoration of the neutrophil deficiency by administration of the HL-60 cell line will enable the individual to mount a neutrophil mediated host defense against and resolve the underlying infection.

The irradiated and activated HL-60 cell line of the invention can be used in a method for treating hematogenously disseminated fungal infection in an individual if administered in an effective amount. In a related embodiment an effective amount of an irradiated and activated HL-60 cell line of the invention can be transfused in a method for treating neutropenia in an individual.

Monoclonal antibodies useful in conjunction with the present invention are those that are specific for a targeted microbial species. In preferred embodiments, the monoclonal antibodies are operatively attached to the phagocytes. For the purposes of this disclosure, the a monoclonal antibody refers to one or more monoclonal antibodies derived from a single clone of a B lymphocyte. Furthermore, as used herein, the monoclonal antibody and phagocyte are operatively attached via a chemical bond, either covalent or ionic. The antibody is selected based on having a site that will recognize and bind with a complementary site on the surface of the cell of at least the targeted microbial pathogen In one embodiment of the invention, a homing molecule, such as an antibody of fragment thereof, can be used to target the phagocytes to the microbe. In order to maximize the ability of the cell-line to kill *C. albicans*, a subpopulation of the HL-60 cell-line will be genetically targeted to a fungal-specific antigen. Targeting of *C. albicans* via an exogenous antibody has been shown to markedly increase killing of the fungus as exemplified herein and by van Spriel A B et al. *J Infect Dis* 1999; 179(3):661-9; Caesar-TonThat et al. *Infect Immun* 1997; 65(12):5354-7, and Valerius et al. *Blood* 1997; 90(11):4485-92, all of which are incorporated herein by reference in their entirety.

An effective amount of the therapeutic composition is determined based on the intended goal. The quantity to be administered, both according to number of treatments and unit dose, depends on the protection desired. Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

The therapeutic compositions of the invention are provided to an individual having a microbial infection in an amount sufficient to exert a microcidal or microstatic effect. A microstatic effect means a prevention of an increase in the number of susceptible pathogenic organisms while a microcidal effect refers to a clinically significant reduction in the number of susceptible pathogenic organisms. A therapeutically effective amount of a composition of the invention is that which is microstatically effective and/or microcidally effective. The compositions provided by the invention are effective as antibacterial compositions, antifungal compositions, antiprotozoal compositions, antiviral compositions and mixtures thereof.

In a preferred embodiment, the therapeutic compositions of the invention are provided to a patient having a fungal infection in an amount sufficient to exert a fungicidal or fungistatic effect upon fungi contacted by the composition. It will be understood with benefit of this disclosure that such dosages may vary considerably according to the patient, the infection presented by the patient, and the particular active ingredients comprising the therapeutic composition. In general, $1.5 \times 10^9$ cells/kg are a suitable target dose that would mimic the normal, endogenous turnover rate in infected individuals. Methods for determining appropriate target doses for treatment of infections are well known in the art and can be ascertained by the skilled person. Such methods are described by Craddock et al., *Annals of Internal Medicine*. 52:281-294 (1960); Athens et al., *Journal of Clinical Investigation*. 40:989-995 (1961); Athens et al, *Journal of Clinical Investigation* 44:778-788 (1965); Marsh et al., *J Clin Invest*. 1967; 46:1943-1953 (1967); Dancey et al., *J Clin Invest*. 58:705-715 (1976).

In one embodiment of the invention, a homing molecule, such as an antibody of fragment thereof, can be used to target the phagocytes to the fungus. In order to maximize the ability of the cell-line to kill *C. albicans*, we intend to genetically target a subpopulation of the HL-60 cell-line to a fungal-specific antigen. Targeting of *C. albicans* via an exogenous antibody has been shown to markedly increase killing of the fungus as exemplified herein and by van Spriel A B et al. *J Infect Dis* 1999; 179(3):661-9; Caesar-TonThat et al. *Infect*

*Immun* 1997; 65(12):5354-7, and Valerius et al. *Blood* 1997; 90(11):4485-92, all of which are incorporated herein by reference in their entirety.

When administration of the compositions of the present invention via transfusion is the preferred route, the therapeutic compositions of the present invention should administered gradually over a period of time ranging from 0.001 h to 100 h. More preferably, when administration of the therapeutic compositions of the present invention via transfusion is the preferred route, the therapeutic compositions of the present invention should administered gradually over a period of time ranging from 0.1 h to 50 h. Most preferably, when administration of the therapeutic compositions of the present invention via infusion is the preferred route, the therapeutic compositions of the present invention should administered gradually over a period of time ranging from 1 h to 10 h.

Thus, the various embodiments of the invention are based, in part, on the discovery of a novel cell-based immunotherapy that recapitulates neutrophil functions in neutropenic, individuals afflicted with an infection. Administration of activated, irradiated HL-60 cells results in enhanced clearance of tissue microbial burden and improved survival.

It is understood that modifications which do not substantially affect the activity the various embodiments of this invention are also provided within the definition of the invention provided herein. Accordingly, the following examples are intended to illustrate but not limit the present invention.

EXAMPLE I

Shortened Activation of HL-60 Cells Resulted in Equivalent to Superior Killing of *C. albicans*

This example demonstrated that shortened activation of HL-60 cells can result in superior candidacidal activity.

As a marker of safety, HL-60 cells and cell supernatant were tested commercially (Focus Laboratories, Cypress, Calif.) for a variety of human pathogenic viruses (Table 1). No evidence of viral infection was found.

TABLE 1

No evidence of common viruses in HL-60 cells.

| Virus | Test | Result |
| --- | --- | --- |
| HTLV 1 | PCR | Not detected |
| HTLV 2 | PCR | Not detected |
| HCV | RT-PCR | Not detected |
| HBV | PCR | Not detected |
| HIV | Ultrasensitive RT-PCR | Not detected |
| HHV-6 | PCR | Not detected |
| HHV-7 | PCR | Not detected |
| VZV | PCR | Not detected |
| CMV | PCR | Not detected |
| EBV | PCR | Not detected |

HTLV = human T lymphocyte virus; HCV = hepatitis C virus; HBV = hepatitis B virus; HIV = human immunodeficiency virus; HHV = human herpes virus; VZV = varicella zoster virus; CMV = cytomegalovirus; EBV = Epstein Barr virus It was previously reported that activation of HL-60 cells for seven days in the presence of RA and DMSO resulted in superior fungicidal activity compared to activation with either compound alone. Spellberg et al., *J Leukoc Biol.* 78:338-344 (2005).

Briefly, for the experiments described herein, HL-60 cells (American Type Culture Collection, Rockville, Md.) were cultured at 37° C. in 5% $CO_2$ in RPMI 1640 supplemented with glutamine (Irvine Scientific, Santa Ana, Calif.), 10% fetal bovine serum (Gemini BioProducts, Woodland, Calif.), 1% penicillin, streptomycin, and glutamine (Gemini Bio-Products), and 50 μM β-mercaptoethanol (Sigma-Aldrich, St. Louis, Mo.). HL-60 cells were activated by incubation in the presence of 1.3% (v/v) DMSO and 2.5 μM RA (both from Sigma-Aldrich). For harvesting, cells were centrifuged at 250 g, washed in PBS (Irvine Scientific), and resuspended at the appropriate concentration. The conditioned media of activated HL-60 cell cultures was washed in parallel for use as placebo for in vivo treatment. To wash the conditioned media, the media was centrifuged, decanted, and PBS was added to the residua at an equivalent volume to the final HL-60 cell suspension.

In some experiments, HL-60 cells were irradiated with high energy X-rays by exposure to $^{137}$cesium chloride in a JL Sheppard & Associates irradiator (Model 143-45) in the clinical blood bank laboratory at Harbor-UCLA Medical Center. Radiation doses were confirmed using thermoluminescent dosimetry chips (Global Dosimetry Solutions, Inc., Irvine, Calif.).

To quantify the candidacidal effect of HL-60 cells, a previously described killing assay was utilized as described in 20 In brief, $8 \times 10^4$ phagocytes were co-cultured with $4 \times 10^3$ *C. albicans* (20:1 ratio) for 4 h at 37° C. in RPMI+10% pooled human serum (Sigma). At the end of the incubation, the cultures were sonicated, serially diluted, overlaid with YPD agar, and incubated overnight at 37° C. CFUs were counted to assess killing of *C. albicans*, compared to control cultures of *Candida* alone with no HL-60 cells.

To quantify cell proliferation, tritiated thymidine (Amersham Biosciences, Irvine, Calif.) was added to HL-60 cell cultures. Eighteen hours later, the cells were harvested on filter paper using a Combi Cell Harvester (Molecular Devices, Sunnyvale, Calif.). The filter paper was dissolved in scintillation fluid, and radioactive counts were determined in a β-counter.

To determine if shorter periods of dual activation similarly stimulated HL-60 fungicidal effects while improving viability, HL-60 cells were activated for one, three, or seven days in RA plus DMSO. All three activation strategies resulted in superior killing of *C. albicans* by HL-60 cells as compared to unactivated HL-60 cells (FIG. 1).

FIG. 1 thus demonstrates that shorter duration of HL-60 activation results in significant killing of *C. albicans*. For the results shown in FIG. 1, HL-60 cells were activated with retinoic acid (RA) and dimethylsulfoxide (DMSO) for 1, 3, or 7 days. Unactivated or activated HL-60 ($8 \times 10^4$ cells) were incubated with *C. albicans* ($4 \times 10^3$) at a 20:1 ratio for 4 hours. Results shown in FIG. 1 are from a minimum of 3 separate experiments run in triplicate. * $p<0.05$ vs. Unactivated and ‡ $p<0.007$ vs all other groups by Steel test for non-parametric multiple comparisons.

Activation for three days resulted in superior killing compared to all other groups. Given the ≥90 loss in HL-60 cell viability following seven day activation (Spellberg et al., *J Leukoc Biol.* 78:338-344 (2005), and the impracticality of waiting seven days for activation to occur, further investigations focused on the one and three day activation strategies.

EXAMPLE II

Viability and Flow Cytometric Parameters Reliably Distinguish Unactivated from Activated HL-60 Cells This example demonstrated that unactivated HL-60 cells can be reliably distinguished from activated HL-60 cells by viability and flow cytometry.

Given the need to ensure adequate activation of HL-60 cells from experiment to experiment, several cellular parameters were explored as potential quality-control markers of activation. Concordant with prior results using seven day activated cells (Spellberg et al., *J Leukoc Biol.* 78:338-344 (2005), it was found that continuous activation of the cells in the presence of RA and DMSO resulted in differentiation of the cells and a progressive decrease in cell viability starting after day one of activation. By day three of activation, HL-60 cell viability was significantly and reliably decreased as compared to unactivated and one day activated cells (FIG. 2a).

During cell counting, it was noted that activated HL-60 cells appeared smaller than unactivated HL-60 cells. This significant change in size was confirmed by flow cytometry (forward side scatter) for three day, but not one day, activated HL-60 cells compared to unactivated cells (FIG. 2b, Table 2).

Figure 2:
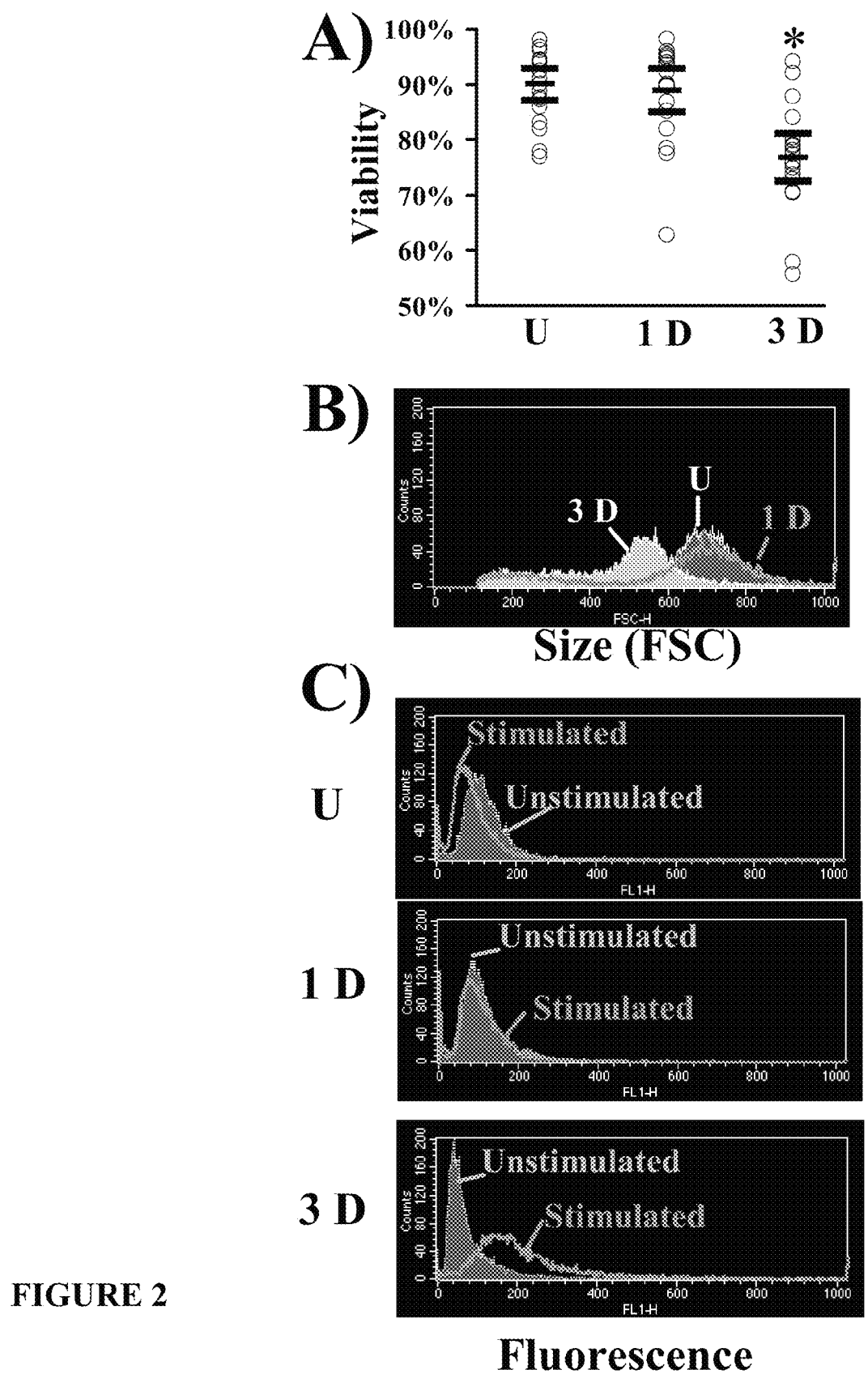
FIG. 2 demonstrates that viability and flow cytometric parameters distinguish unactivated from activated HL-60 cells.

Thus, FIG. 2 demonstrates that viability and flow cytometric parameters distinguish unactivated from activated HL-60 cells. HL-60 cells were activated with RA and DMSO for 1 or 3 days (1 D, 3 D). A) Viability was determined by trypan blue exclusion. N=22 samples per group. Upper and lower bars reflect interquartile ranges; middle bar reflects the median. *p<0.05 compared to U and 1D by Steel test. B) Size of cells determined by forward side scatter. C) Oxidative burst as determined by DHR fluorescence either in the absence (unstimulated) or presence (stimulated) of PMA. Results are representative of six experiments.

Prior to PMA stimulation, unactivated HL-60 cells had significantly greater oxidative activity than did three-day activated, but not one-day activated, HL-60 cells (FIG. 2b, Table 2). In contrast, PMA stimulation resulted in a marked increase in oxidative activity in three day activated HL-60 cells, but not in unactivated or one day activated HL-60 cells (FIG. 2b, Table 2).

EXAMPLE III

Flow Cytometric Parameters can Predict HL-60 Cell Candidacidal Capacity

This example demonstrates that flow cytometric parameters correlate with HL-60 candidacidal capacity.

To determine if the parameters that distinguished unactivated from activated HL-60 cells correlated with candidacidal capacity, the above cellular parameters were measured before performing kill assays with the same cells. Cell viability, cell size, and change in cell size during activation all inversely correlated with anti-candidal activity, regardless of whether all groups were compared or just unactivated versus three-day activated cells were compared (FIG. 3).

Figure 3:
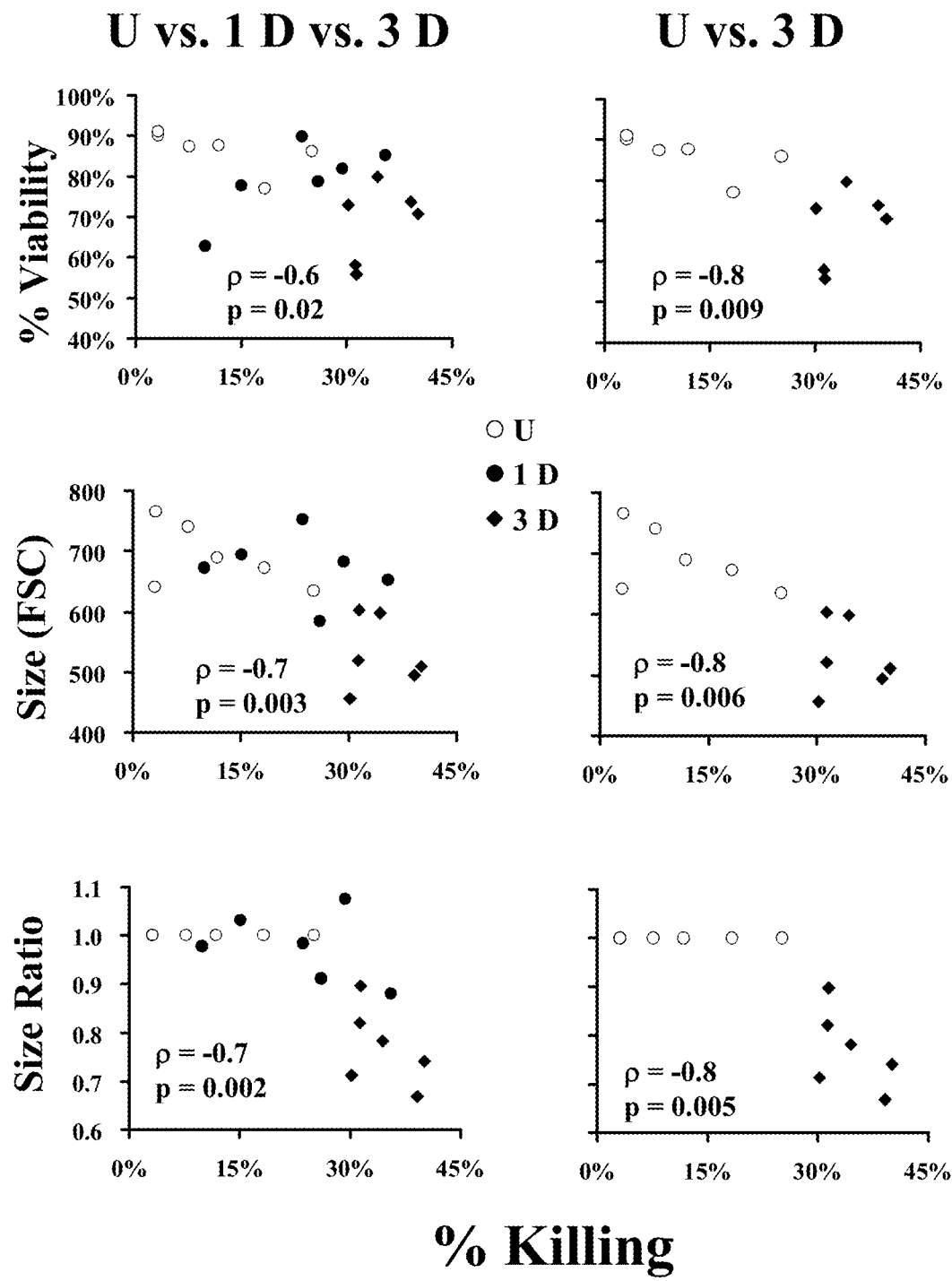
FIG. 3 demonstrates that HL-60 viability and cell size correlate with anti-candidal killing activity.

FIG. 3 demonstrates that HL-60 viability and cell size correlate with anti-candidal killing activity. Immediately prior to performing anti-*C. albicans* kill assays, viability (trypan blue exclusion) and flow cytometry parameters were

TABLE 2

Quality Control Results

| Parameter | U* | 1 D* | 3 D* | Comparisons with $P \leq 0.05$ |
|---|---|---|---|---|
| Forward Side Scatter (FSC) | 681 (728, 649) | 678 (690, 657) | 515 (579, 499) | 3 D vs. U; p = 0.01<br>3 D vs. 1; p = 0.03 |
| ‡ΔFSC—PMA Stimulation | 0.6 (0.9, 0.4) | 0.5 (0.9, 0.3) | 0.6 (0.8, 0.5) | None |
| Median Fluorescence | 124 (138, 106) | 104 (114, 89) | 59 (64, 55) | 3 D vs. U; p = 0.03 |
| ‡ΔMedian Fluorescence—PMA Stimulation | 0.7 (0.7, 0.6) | 0.9 (1.0, 0.6) | 2.3 (2.9, 1.6) | 3 D vs. U; p = 0.03<br>3 D vs. 1; p = 0.03 |
| % Cells Fluorescent | 5.0 (8.4, 2.2) | 2.0 (3.3, 0.9) | 1.0 (1.1, 0.9) | 3 D vs. U; p = 0.01 |
| ‡Δ % Cells Fluorescent—PMA Stimulation | 0.3 (0.7, 0.2) | 1.2 (1.7, 0.7) | 13.5 (20.5, 5.3) | 3 D vs. U; p = 0.03 |

*Median ($75^{th}$ quartile, $25^{th}$ quartile)
‡Δ = ratio comparing cells without PMA stimulation to cells with PMA stimulation;
Statistics by non-parametric Steel test for multiple comparisons.

Oxidative burst capacity of unactivated and activated HL-60 cells was quantified in the presence or absence of PMA by using DHR-fluorescence.

To determine the degree of activation of HL-60 cells, a modification of the method of Roesler et al. was utilized as described in Roesler and Emmendorffer, *Blood* 78:1387-1389 (1991); Roesler et al., *Eur J. Pediatr.* 1991; 150:161-165 (1991). This technique relies upon the induction of fluorescence of dihydrorhodamine (DHR) in the presence of reactive oxygen intermediates, and is utilized clinically to diagnose Chronic Granulomatous Disease. In brief, unactivated or activated HL-60 cells were incubated in the dark at 37° C. for 20 minutes in the presence or absence of 50 μg/ml of phorbol myristate acetate (PMA, Sigma-Aldrich) and 100 μM DHR 123 (Molecular Probes, Eugene, Oreg.). The cells were then analyzed for size and fluorescence with a Becton-Dickinson FACScan instrument (Becton Dickinson, San Jose, Calif.) using FACSComp software per the manufacturer's recommendations. During acquisition, photomultiplier amplitudes were set based on negative control cells that were cultured with or without DHR, and without PMA (unstimulated).

determined on Unactivated (U) HL-60 cells or HL-60 cells activated with RA and DMSO for 1 or 3 days (1D, 3 D). Size ratio indicates the size of 1 or 3 day activated cells divided by the size of unactivated cells. Results are from six experiments, with % killing reflecting triplicate values from each experiment. Rho (ρ) and p values were determined by the non-parametric Spearman correlation test.

Figure 4:
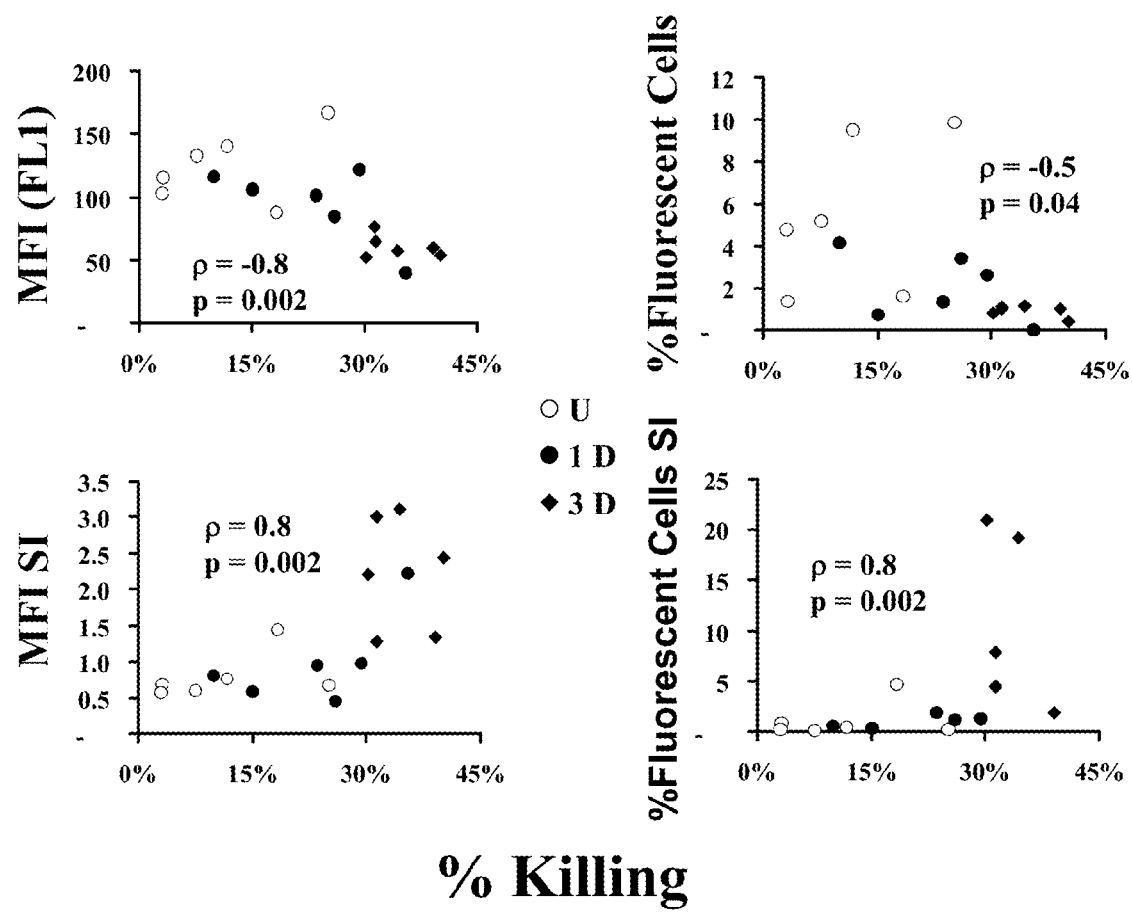
FIG. 4 demonstrates that modified phagoburst activity correlates with anti-candidal killing of HL-60 cells.

Similarly the mean fluorescence intensity of HL-60 cells prior to PMA stimulation inversely correlated with killing (ρ=−0.8 and p=0.002 for all groups; ρ=−0.7 and p=0.02 for unactivated vs. three-day activated), as did the percent of fluorescent cells (ρ=−0.5 and p=0.04 for all groups; ρ=−0.5 and p=0.08 for unactivated vs. three-day activated)(FIG. 4). In contrast, following PMA stimulation, the change in fluorescence (ρ=0.8 and p=0.002 for all groups; ρ=0.8 and p=0.01 for unactivated vs. three-day activated) and change in percent fluorescent cells (ρ=0.8 and p=0.002 for all groups; ρ=0.6 and p=0.04 for unactivated vs. three-day activated) both positively correlated with anti-candidal killing (FIG. 4).

FIG. 4 demonstrates that modified phagoburst activity correlates with anti-candidal killing of HL-60 cells. Median fluorescence intensity (MFI) in channel FL1 and % fluorescent cells were determined. SI=stimulation index, which is a ratio of signal from HL-60 cells after stimulation with PMA divided by the signal from unstimulated cells. Results are from six experiments, with % killing reflecting the mean of triplicate values from each experiment. As above, Rho ($\rho$) and p values determined by the non-parametric Spearman correlation test.

Statistical results described in this application were obtained by pair-wise comparison of Kaplan-Meier curves with the non-parametric Log Rank test. In vitro killing and replication and in vivo tissue fungal burden were compared with the non-parametric Steel test for multiple comparisons (Rhyne and Steel R G, *Biometrics*. 23:539-549 (1967), or the Wilcoxon Rank Sum test, as appropriate.

EXAMPLE IV

Irradiation Abrogates HL-60 cell Replication Without Impairing Anti-Candidacidal Capacity This example demonstrates that irradiation abrogates HL-60 replication without impact on either the anti-candidacidal effects of the HL-60 cells or on the accuracy of cell size or cell fluorescence as quality control markers for successful activation of HL-60 cells.

To mitigate any long-term risk of infusing an immortal cell line into a neutropenic host, the impact of irradiation on cell replication and anti-candidal capacity was determined. Irradiation with 2100+/−300 rads resulted in a marked decrease in cell replication in unactivated or one- or three-day activated HL-60 cells (FIG. 5a). This decline in replication became progressively greater between days one to three following the irradiation. In contrast, seven day activated HL-60 cells already had a very low replicative capacity that was not significantly lowered further by irradiation. Irradiation had no significant impact on the anti-candidacidal effects of the HL-60 cells (FIG. 5b).

Figure 5:
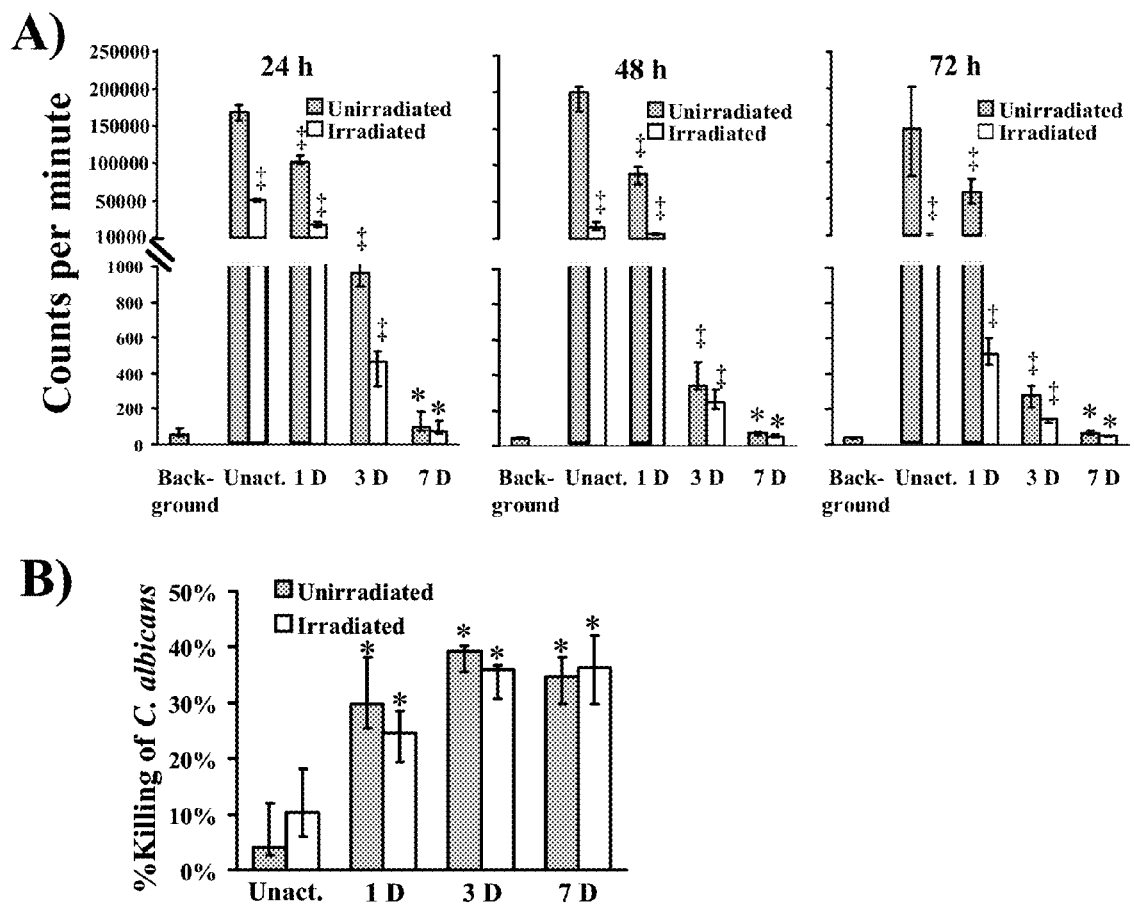
FIG. 5 demonstrates that irradiation abrogates replication while sparing anti-candidal effects of HL-60 cells.

Overall, FIG. 5 demonstrates that irradiation abrogates replication while sparing anti-candidal effects of HL-60 cells. HL-60 cells were activated with RA and DMSO for 1, 3, or 7 days (1 D, 3 D, 7 D). Unactivated or activated cells were then irradiated with 2100+/−300 rads. Kill assays were performed with either irradiated or unirradiated cells. The same batches of cells were cultured for an additional 24, 48, or 72 h following irradiation prior to determination of replication activity. Results are from four experiments, performed in duplicate for replication or triplicate for killing. ‡ $p<0.05$ vs. both unactivated unirradiated cells and background, and * $p<0.05$ vs. unactivated unirradiated cells by the non-parametric Steel test for multiple comparisons.

Figure 6:
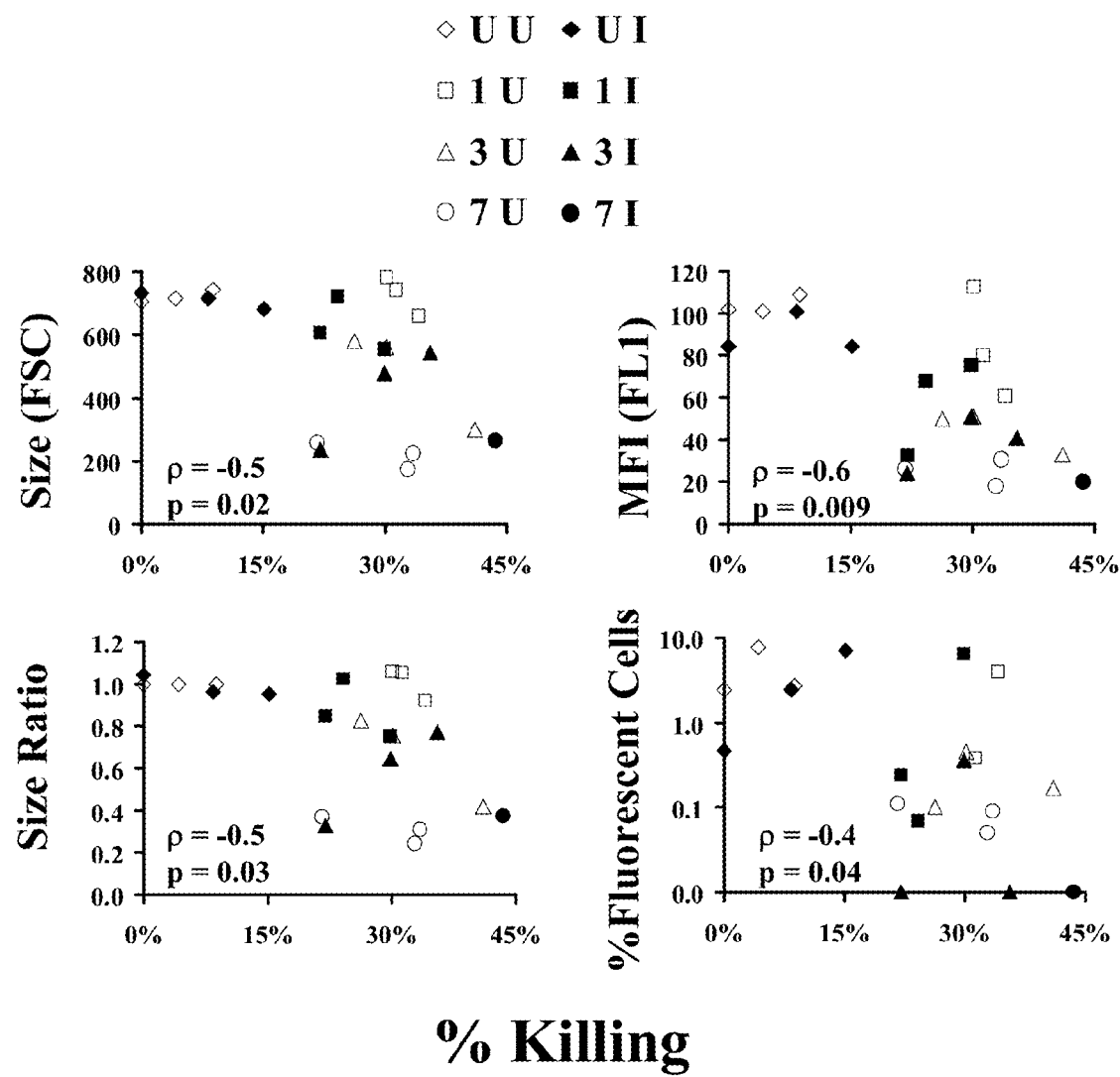
FIG. 6 demonstrates that irradiation does not alter the accuracy of several quality control markers of HL-60 cell activation.

FIG. 6 demonstrates that irradiation does not alter the accuracy of several quality control markers of HL-60 cell activation. In particular, irradiation had no impact on the accuracy of cell size or cell fluorescence as quality control markers for successful activation of HL-60 cells. Median fluorescence intensity (MFI) in channel FL1 and % fluorescent cells were measured in HL-60 cells. Ratio refers to size of HL-60 cells activated with RA and DMSO divided by the size of unactivated HL-60. Results are from three experiments, with % killing reflecting the mean of triplicate values from each experiment. Rho ($\rho$) and p values determined by the non-parametric Spearman correlation test.

EXAMPLE V

Activated Irradiated HL-60 Cells Improved Survival of Neutropenic, Candidemic Mice by Reducing Tissue Fungal Burden This example demonstrates that activated irradiated HL-60 cells improve survival of neutropenic, candidemic mice by reducing tissue fungal burden.

It was previously found that treatment with HL-60 cells activated with RA+DMSO for seven days resulted in approximately 50% survival in an otherwise 100% lethal, neutropenic murine model of candidemia.

To determine if the shortened activation regimen was similarly effective, mice were made neutropenic with cyclophosphamide and infected via the tail-vein with *C. albicans*, as previously described by Spellberg et al., *J Leukoc Biol.* 78:338-344 (2005). Mice were treated with placebo, or one or three day activated HL-60 cells that were either irradiated or unirradiated. Treatments were administered iv via the tail vein starting one hour after infection and again on days two, four, and six after infection. Mice treated with irradiated, one or three day activated HL-60 cells had significantly improved survival compared to all other treatment regimens (FIG. 7A). However, only treatment with three day activated, irradiated HL-60 cells resulted in long-term survival.

Male Balb/c mice (20-25 g) were obtained from the National Cancer Institute (Frederick, Md.). Mice were made neutropenic by a single intraperitoneal (ip) injection of cyclophosphamide (230 mg/kg). Van t Wout et al., *Antimicrob Agents Chemother*. 33:147-151 (1989). In pilot studies in which peripheral blood leukocytes were manually counted, this treatment regimen resulted in pancytopenia from day 1 through 7 post-cyclophosphamide treatment (days 0 through 6 post-infection given infection on day 1 post-cyclophosphamide), with recovery of cell counts beginning on day 8 post-cyclophosphamide (day 7 post-infection). Mice were infected via the tail-vein with 0.2 ml of PBS containing $5\times10^4$ blastoconidia of *C. albicans* approximately 32 h after cyclophosphamide injection, as previously described by Spellberg et al., *Infect Immun*. 71:5756-5764 (2003).

Treatment with $1.5\times10^7$ HL-60 cells/mouse (~$7.5\times10^8$ cells/kg) or placebo in 0.25 ml of PBS were administered via the tail-vein 30-60 minutes after infection on day 0, and again on days 2, 4, and 6 post-infection. All procedures involving mice were approved by the institutional animal use and care committee, following the National Institutes of Health guidelines for animal housing and care.

For murine infections, *Candida albicans* SC5314, a well-characterized clinical isolate described in Spellberg et al., *J Leukoc Biol*. 78:338-344 (2005) and Spellberg et al., *Infect Immun*. 71:5756-5764 (2003), that is highly virulent in animal models, was serially passaged three times in yeast peptone dextrose broth (YPD, Difco) and washed twice with PBS. Infectious inocula were prepared by counting in a hemacytometer.

It was previously reported that seven day activated HL-60 cells enhanced clearance of *C. albicans* from target organs in vivo. Spellberg et al., *J Leukoc Biol*. 78:338-344 (2005). To confirm that activated, irradiated HL-60 cells similarly enhanced clearance of the fungus from neutropenic mice, tissue fungal burden was determined in mice treated with placebo or one or three day activated, irradiated HL-60 cells.

Neutropenic mice were infected and treated as described above, however on day five post-infection (after 3 treatment doses, on the day when placebo-treated mice were anticipated to begin dying) mice were euthanized and their kidneys homogenized and quantitatively cultured. Kidneys were utilized because they are the predominant target organ of infection during murine candidemia as described in Spellberg et al., *J Leukoc Biol.* 78:338-344 (2005); Spellberg et al., *Infect Immun.* 71:5756-5764 (2003); Spellberg et al., *J Infect Dis.* In press (2005); Brieland et al., *Infection and Immunity* 69:5046-5055 (2001); Netea et al., *J Immunol.* 163:1498-1505 (1999); Clemons and Stevens, *J Antimicrob Chemother.* 47:183-186 (2201); Louria D B. "*Candida* infections in experimental animals" in *Candidiasis.* New York: Raven Press (Bodey G P, Fainstein V, eds.) 29-51 (1985). Treatment with either one or three-day activated, irradiated HL-60 cells resulted in approximately 0.7 log CFU/g reduction in kidney fungal burden (FIG. 7B).

Figure 7:
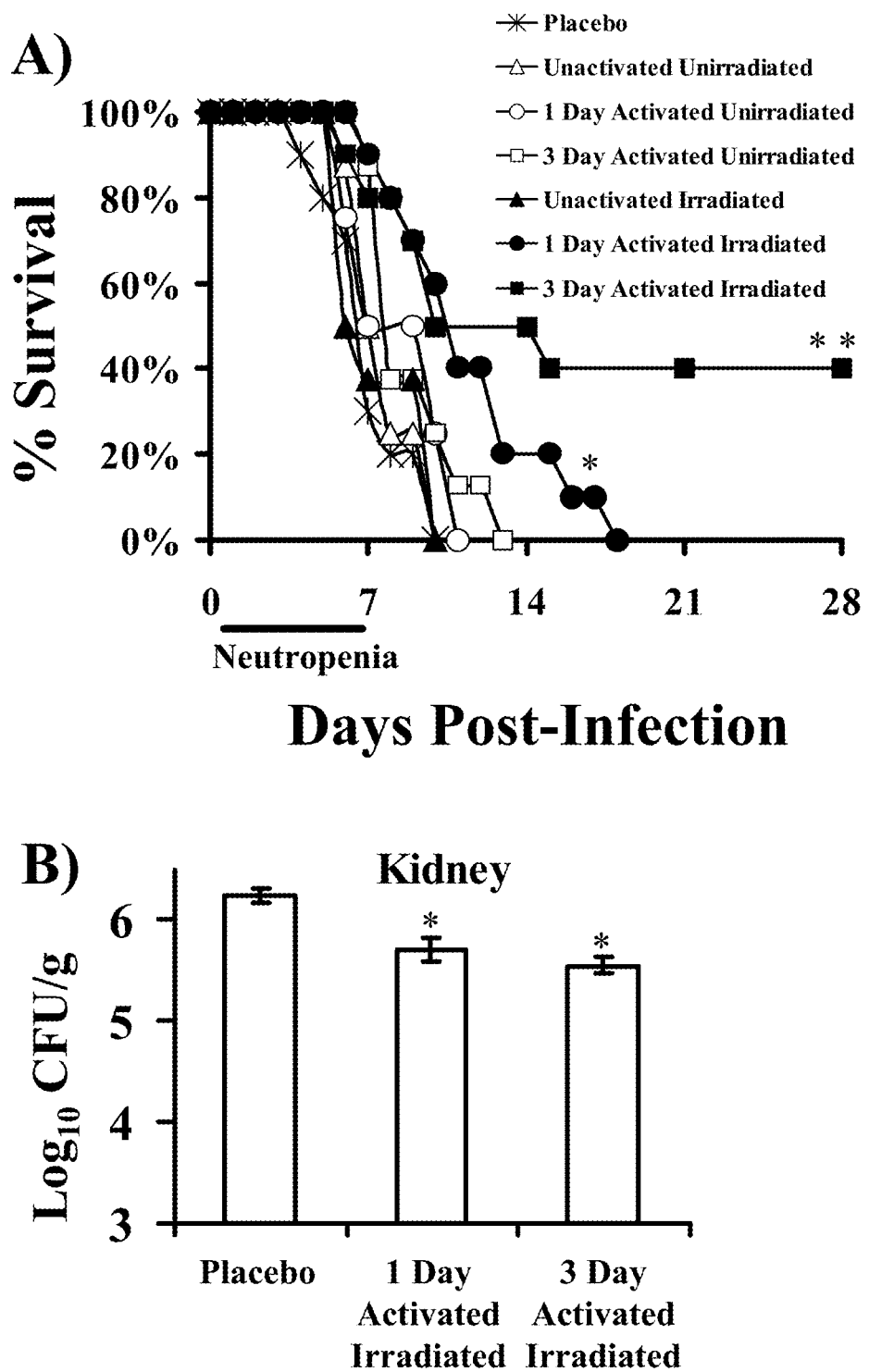
FIG. 7 demonstrates that activated, irradiated HL-60 cells improve survival of and reduce tissue fungal burden in candidemic, neutropenic mice.

FIG. 7 demonstrates that activated, irradiated HL-60 cells improve survival of and reduce tissue fungal burden in candidemic, neutropenic mice. For the results in panel (A) Male Balb/c mice (n=10 from 2 experiments) were made neutropenic with cyclophosphamide and infected via the tail-vein with $5 \times 10^4$ blastospores of *C. albicans*. HL-60 cells were administered iv via the tail-vein on days 0, 2, 4, and 6 post-infection. *p<0.05 vs. all groups except 3 Day Activated Unirradiated & Irradiated; **p<0.05 vs. all groups except 1 Day Activated Irradiated (p=0.16), by Log Rank test. For the results in panel (B) Day 5 kidney fungal burden (n=8 mice per group) in candidemic, neutropenic mice treated with HL-60 cells or placebo on days 0, 2, and 4 post-infection. Y axis reflects lower limit of detection of the assay. *p<0.05 vs. placebo by non-parametric Steel test for multiple comparisons.

To determine if HL-60 cell therapy resulted in any end-organ toxicities, tissue histopathology was evaluated on day five post-infection in a variety of organs, including brain, heart, lung, sternum (for bone marrow), spleen, liver, and kidneys. Compared to mice treated with placebo, there was no discernable toxicity found in any organ.

Overall, the preceding examples demonstrate that seven day activation of HL-60 cells resulted in a virtual complete abrogation of HL-60 cell replication, whereas activation for shorter periods of time significantly reduced replication but did not abrogate it completely. However, the combination of cell irradiation and activation for three days resulted in replication rates that were similar to seven days of activation. Irradiated, one day activated cells had replication rates that were higher than irradiated, three day activated cells. Although treatment of candidemic, neutropenic mice with irradiated, one day activated HL-60 cells did statistically improve the time to death compared to placebo, the irradiated, one day activated cells did not result in long-term survival. These data suggest that continued replication of HL-60 cells abrogates their protective effect. Despite intensive investigation to identify an organ-specific toxicity mediated by replicating HL-60 cells, no specific toxicity could be found by organ histopathology. Nevertheless, our prior studies convincingly demonstrated that unactivated HL-60 cells were toxic to mice, whereas cells activated for seven days were not.

Several facile markers were identified, as described above, that reliably distinguished activated from unactivated HL-60 cells. These markers, including cell viability, cell size, and oxidative free radical formation, correlated with in vitro killing of *C. albicans*, making them useful quality control markers of activation. It has been previously reported that differentiation of HL-60 cells with DMSO results in a steady acquisition of oxidative burst capacity when the cells are exposed to PMA. Hua et al., *J Leukoc Biol.* 68:216-224 (2000).; Collins et al., *J Exp Med.* 149:969-974 (1979). However, surprisingly, we found that in the absence of PMA, undifferentiated HL-60 cells had greater capacity to produce oxygen free radicals than DMSO plus RA-activated HL-60 cells. This production of oxygen free radicals by undifferentiated HL-60 cells appeared to be the result of dysregulation, because the free radical production was actually suppressed by stimulation of the cells with PMA. In contrast, normal phagocytes do not produce oxygen free radicals in the resting state, and only do so after stimulation with a cell activator, such as PMA or f-Met-Leu-Phe. Akin to normal phagocytic function, differentiation of HL-60 cells with DMSO plus RA completely suppressed oxygen free radical production at baseline, but enabled a massive increase in oxygen free radical production when the cells were stimulated with PMA.

In summary, a combination of low dose irradiation with dual RA and DMSO activation of HL-60 cells resulted in a marked increase in candidacidal capacity, a virtually total abrogation of cell replication, and a marked improvement in the survival of neutropenic, candidemic mice.

EXAMPLE VI

Activated HL-60 Cells have Antibacterial Capacity

This example demonstrates that irradiation does not diminish the capacity for activated HL-60 cells to kill multi-drug resistant *P. aeruginosa* or methicillin-resistant *S. aureus* (MRSA).

Figure 8:
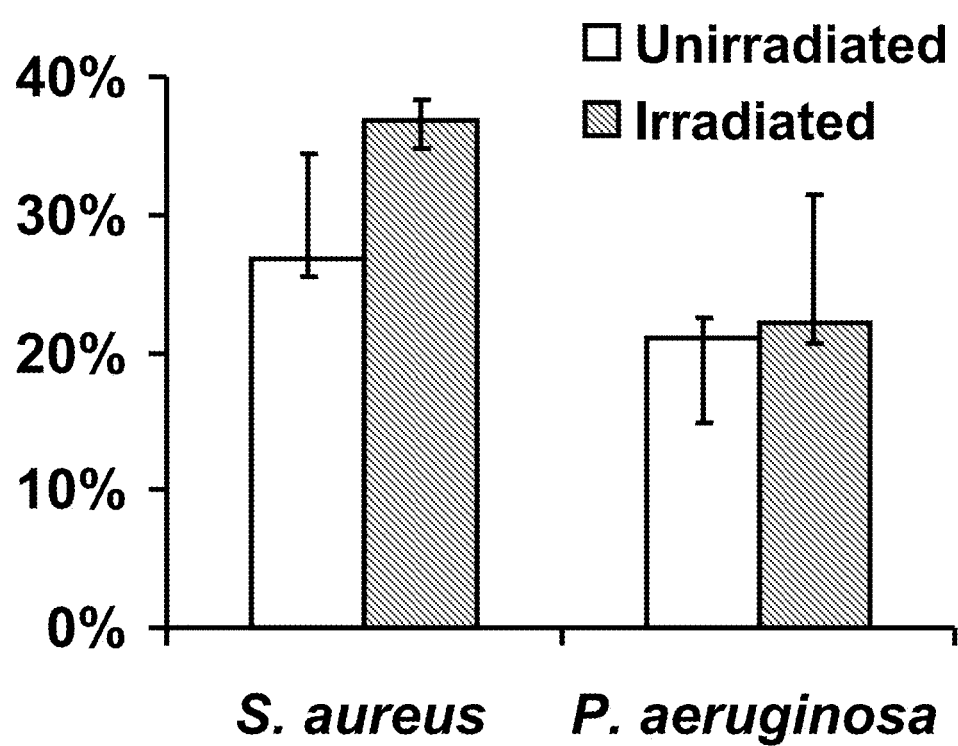
FIG. 8 shows that irradiation does not diminish the capacity for activated HL-60 cells to kill multi-drug resistant *P. aeruginosa* or methicillin-resistant *S. aureus* (MRSA).

For the results shown in FIG. 8, HL-60 cells were activated in the presence of DMSO and retinoic acid for 3 days. Activated HL-60 cells were irradiated (approximately 2000 rads) or not, and were incubated for 2 hours in the presence of either *P. aeruginosa* or MRSA (10:1 ratio of cells to bacteria). Control cultures included equivalent numbers of bacteria with no HL-60 cells. After 2 hours, the cultures were sonicated, diluted, and plated in tryptic soy agar. Percent killing was calculated as the reduction in CFUs in cultures with HL-60 compared to the cultures without HL-60. Results are from three experiments each performed in triplicate.

Throughout this application various publications have been referenced within parentheses. The disclosures of these publications in their entireties are hereby incorporated by reference in this application in order to more fully describe the state of the art to which this invention pertains.

It is understood that modifications which do not substantially affect the activity of the various embodiments of this invention are also included within the definition of the invention provided herein. Those skilled in the art will readily appreciate that the specific examples and studies detailed above are only illustrative of the invention. Accordingly, specific examples disclosed herein are intended to illustrate but not limit the present invention. It also should be understood that, although the invention has been described with reference to the disclosed embodiments, various modifications can be made without departing from the spirit of the invention. Accordingly, the invention is limited only by the following claims.

We claim:

1. A method for treating hematogenously disseminated fungal infection in a neutropenic individual, said method comprising transfusion of an effective amount of an activated and irradiated HL-60 cell line to an individual afflicted with a hematogenously disseminated fungal infection, wherein the fungal infection is candidiasis.

2. The method according to claim 1, wherein the candidiasis is caused by *Candida albicans*.

3. The method of claim 1, wherein said HL-60 cell line was activated for a duration of at least a three days.

4. The method of claim 3, wherein said HL-60 cell line was activated in the presence of retinoic acid (RA) and dimethylsulfoxide (DMSO).

5. The method of claim 1, wherein said HL-60 cell line was irradiated with at least 1500 rads.

6. The method of claim 1, wherein said HL-60 cells have no replicative capacity.

\* \* \* \* \*